(12) United States Patent
Chen et al.

(10) Patent No.: US 11,744,804 B2
(45) Date of Patent: Sep. 5, 2023

(54) MICROCAPSULE POWDER STABLE IN GASTRIC ACID, METHOD FOR PREPARING SAME, AND USE THEREOF

(71) Applicant: HOBOOMLIFE BIO-TECHNOLOGY (SHENZHEN) CO., LTD., Guangdong (CN)

(72) Inventors: Jiansheng Chen, Guangdong (CN); Bo Zhang, Guangdong (CN); Tong Zhang, Guangdong (CN); Yaying Hou, Guangdong (CN); Jing Lv, Guangdong (CN)

(73) Assignee: HOBOOMLIFE BIO-TECHNOLOGY (SHENZHEN) CO., LTD., Guangdong (CN)

( * ) Notice: Subject to any disclaimer, the term of this patent is extended or adjusted under 35 U.S.C. 154(b) by 0 days.

(21) Appl. No.: 18/059,470

(22) Filed: Nov. 29, 2022

(65) Prior Publication Data
US 2023/0087524 A1    Mar. 23, 2023

Related U.S. Application Data

(63) Continuation of application No. PCT/CN2022/088327, filed on Apr. 22, 2022.

(30) Foreign Application Priority Data

Jul. 20, 2021    (CN) .......................... 202110819545.5

(51) Int. Cl.
*A61K 9/50*    (2006.01)
*A61K 31/7084*    (2006.01)

(52) U.S. Cl.
CPC .......... *A61K 9/5015* (2013.01); *A61K 9/5089* (2013.01); *A61K 31/7084* (2013.01)

(58) Field of Classification Search
CPC . A61K 9/5015; A61K 9/5089; A61K 31/7084
See application file for complete search history.

(56) References Cited

FOREIGN PATENT DOCUMENTS

| CN | 103251572 A | | 8/2013 |
|---|---|---|---|
| CN | 110237038 A | | 9/2019 |
| CN | 110339179 A | | 10/2019 |
| CN | 113440497 A | * | 9/2021 |
| CN | 115634209 A | * | 1/2023 |

OTHER PUBLICATIONS

Yunyun Wang et al., Pharmaceutical preparation technology, Aug. 2016, p. 362, Chongqing University Press.
Yong Wang et al., Processing of grain and oil by-products, Feb. 2019, pp. 166-167, Jinan University Press.

* cited by examiner

*Primary Examiner* — Shirley V Gembeh
*Assistant Examiner* — Olga V. Tcherkasskaya (57) ABSTRACT

The present invention discloses a microcapsule powder stable in gastric acid, a method for preparing the same and use thereof. The microcapsule powder comprises a core material and a capsule material coated outside the core material, wherein the capsule material has a melting point of greater than 42° C., and the capsule material does not decompose or dissolve under the action of protease and gastric acid, but decomposes under the action of intestinal digestive enzymes. The core material is coated with the capsule material in the microcapsule powder, thus achieving high-efficiency coating of the core material by a single component. The microcapsule powder achieves conventional intragastric stability as well as favorable stability in an open environment at room temperature, thus solving the problem that the conventional embedding solution may only achieve intragastric stability, but the stability in an open environment at room temperature is low.

7 Claims, 2 Drawing Sheets

```
┌─────────────────────────────────────────────────┐
│         Heat a capsule material to melt         │──── S110
└─────────────────────────────────────────────────┘
                        │
                        ▼
┌─────────────────────────────────────────────────┐
│ Fully mix a core material and the melted capsule│
│ material in a heat preservation state to obtain │──── S120
│                  a suspension                   │
└─────────────────────────────────────────────────┘
                        │
                        ▼
┌─────────────────────────────────────────────────┐
│ Perform freeze spray dry granulation on the     │
│ suspension to obtain a required microcapsule    │──── S130
│                    powder                       │
└─────────────────────────────────────────────────┘
```

FIG. 1

```
┌─────────────────────────────────────────────────┐
│ Fully mix a core material and a capsule material│──── S210
│             to obtain a mixture                 │
└─────────────────────────────────────────────────┘
                        │
                        ▼
┌─────────────────────────────────────────────────┐
│ Sequentially perform hot melting and spray      │
│ granulation on the mixture to obtain a required │──── S220
│              microcapsule powder                │
└─────────────────────────────────────────────────┘
```

MICROCAPSULE POWDER STABLE IN GASTRIC ACID, METHOD FOR PREPARING SAME, AND USE THEREOF

CROSS-REFERENCE TO RELATED APPLICATIONS

This application is a continuation of PCT Patent Application No. PCT/CN2022/088327 filed on Apr. 22, 2022, which claims priority to Chinese Patent Application No. 202110819545.5 filed on Jul. 20, 2021, each of which is incorporated herein by reference in its entirety.

TECHNICAL FIELD

The present invention relates to the technical field of food and/or medicine, and in particular relates to a microcapsule powder stable in gastric acid, a method for preparing the same, and use thereof.

BACKGROUND

Reduced nicotinamide adenine dinucleotide (NADH) and reduced nicotinamide adenine dinucleotide phosphate (NADPH), as important physiological substances in the human body, participate in thousands of physiological metabolic reactions in the human body and play an important role in gene repair, immunity improvement, antioxidation, sleep improvement, etc. Adequate NADH or NADPH can better protect the body, prevent and control diseases, and further ensure health. Therefore, in vitro supplement of NADH or NADPH is conducive to promoting various physiological functions of the body to maintain the optimum state. However, NADH and NADPH are biological hydrogens. Light, acidic environment or oxygen and water in the air will damage the molecular structures of NADH and NADPH, resulting in extremely unstable chemical properties (need to be used immediately after preparation). In addition, since NADH and NADPH are acid intolerant, NADH and NADPH taken from outside will lose their activity due to the effect of gastric acid, and therefore the therapeutic effect is difficult to achieve.

In the prior art, NADH and NADPH are generally stabilized by adding antioxidants. However, the method of adding antioxidants cannot ensure that NADH and NADPH do not decompose in the stomach, that is, oral preparations containing NADH or NADPH cannot ensure that NADH or NADPH does not decompose in the stomach in the prior art.

SUMMARY

In view of the prior art, it is necessary to provide a microcapsule powder, a method for preparing the same and use thereof to solve the above problems.

A microcapsule powder stable in gastric acid is provided, including a core material and a capsule material coated outside the core material, wherein the capsule material has a melting point of greater than 42° C., and the capsule material does not decompose or dissolve under the action of protease and gastric acid, but decomposes under the action of intestinal digestive enzymes.

In one example, the capsule material has a melting point of 60-140° C.

In one example, the capsule material is selected from at least one of rice bran fatty alcohols and higher fatty alcohols with an atomic number of carbon (C) of 12 or more.

In one example, a mass ratio of the capsule material to the core material is (70-90):(10-30).

In one example, the capsule material is selected from at least one of octacosanol, triacontanol and dotriacontanol.

In one example, the core material is a substance that is likely to be damaged in gastric juice and needs to be absorbed or take effect in the intestine.

In one example, the core material is selected from at least one of reduced nicotinamide adenine dinucleotide (NADH) and reduced nicotinamide adenine dinucleotide phosphate (NADPH).

In one example, the microcapsule powder has a particle size of 1-1,000 μm.

A method for preparing the microcapsule powder according to the above technical solution is provided, including the following steps:

heating the capsule material to melt, wherein the capsule material has a melting point of greater than 42° C., and the capsule material does not decompose or dissolve under the action of protease and gastric acid, but decomposes under the action of intestinal digestive enzymes;

fully mixing the core material and the melted capsule material in a heat preservation state to obtain a suspension; and performing freeze spray dry granulation on the suspension to obtain the microcapsule powder, wherein the microcapsule powder includes the core material and the capsule material coated outside the core material.

A method for preparing the microcapsule powder according to the above technical solution is provided, including the following steps:

fully mixing the core material and the capsule material to obtain a mixture, wherein the capsule material has a melting point of greater than 42° C., and the capsule material does not decompose or dissolve under the action of protease and gastric acid, but decomposes under the action of intestinal digestive enzymes; and sequentially performing hot melting and spray granulation on the mixture to obtain the microcapsule powder, wherein the microcapsule powder includes the core material and the capsule material coated outside the core material.

A method for preparing the microcapsule powder according to the above technical solution is provided, including the following steps:

heating the capsule material to melt, wherein the capsule material has a melting point of greater than 42° C., and the capsule material does not decompose or dissolve under the action of protease and gastric acid, but decomposes under the action of intestinal digestive enzymes;

mixing the core material and the melted capsule material in a heat preservation state to obtain a mixture;

shearing the mixture in a heat preservation state at a speed of 10,000-16,000 rpm for 6-15 min; and performing spray granulation on the sheared mixture in a condensate liquid to obtain the microcapsule powder, wherein the microcapsule powder includes the core material and the capsule material coated outside the core material.

A method for preparing the microcapsule powder according to the above technical solution is provided, including the following steps:

fully mixing the core material and the capsule material to obtain a mixture, wherein the capsule material has a melting point of greater than 42° C., and the capsule material does not decompose or dissolve under the action of protease and gastric acid, but decomposes under the action of intestinal digestive enzymes; and sequentially performing hot melt extrusion granulation and shearing on the mixture to obtain the microcapsule powder, wherein the shearing speed is 8,000-10,000 rpm, and the microcapsule powder includes the core material and the capsule material coated outside the core material.

Use of the microcapsule powder according to the above technical solution or a microcapsule powder prepared by the preparation method according to the above technical solution in preparation of functional food, health food or medicine is provided.

Compared with the prior art, the present invention has the beneficial effects.

1. In the present invention, the core material is coated with the capsule material. The melting point of the capsule material is defined to be greater than 42° C. and the capsule material does not decompose or dissolve under the action of proteinase and gastric acid, thereby ensuring that the microcapsule powder may not melt, decompose or dissolve in the stomach, and preventing the core material from being released in the stomach. The capsule material decomposes under the action of intestinal digestive enzymes, so that the microcapsule powder decomposes under the action of intestinal digestive enzymes in the intestine, and releases the internal core material after entering the intestine, thereby ensuring that the core material is absorbed or takes effect in the intestine.

2. The microcapsule powder provided by the present invention has favorable stability in an open environment at room temperature, and solves the problem that the conventional embedding solution may only achieve intragastric stability, but the stability in an open environment at room temperature is low.

3. When the capsule material of the present application is used, an unstable core material may be embedded by a single component, whereas the conventional materials for embedding unstable core materials need to be used together with other materials in addition to antioxidants, with various ingredients and complex processes.

4. The microcapsule powder obtained by the present invention has a high product embedding rate and high stability in an open environment at room temperature. Tests show that the microcapsule powder obtained by the present application does not melt, decompose or dissolve in the stomach acid environment, and the core material can be released smoothly in the intestinal environment, thus ensuring that the core material is effectively absorbed by the intestine or fully takes effect in the intestine.

BRIEF DESCRIPTION OF THE DRAWINGS

To describe the technical solutions in embodiments of the present invention or in the existing technology more clearly, the following briefly describes the accompanying drawings required for describing the embodiments or the existing technology. Apparently, the accompanying drawings in the following description show merely some embodiments of the present invention, and a person of ordinary skill in the art may derive other drawings from these accompanying drawings without creative efforts.

DETAILED DESCRIPTION

The following clearly and completely describes the technical solutions in the embodiments of the present invention with reference to the accompanying drawings in the embodiments of the present invention. Apparently, the described embodiments are some of the embodiments of the present invention rather than all of the embodiments. All other embodiments obtained by a person of ordinary skill in the art based on the embodiments of the present invention without creative efforts shall fall within the protection scope of the present invention.

The present invention provides a microcapsule powder stable in gastric acid, including a core material and a capsule material coated outside the core material. The capsule material has a melting point of greater than 42° C., and the capsule material does not decompose or dissolve under the action of proteinase and gastric acid, thereby ensuring that the microcapsule powder does not melt, decompose or dissolve in the stomach, and preventing the core material from being released in the stomach. The capsule material decomposes under the action of intestinal digestive enzymes, so that the microcapsule powder releases the internal core material after entering the intestine, thereby ensuring that the core material is absorbed and takes effect in the intestine.

Preferably, the capsule material has a melting point of 60-140° C.

The melting point of the capsule material being greater than 42° C., preferably 60-140° C., ensures that the capsule material does not melt in the stomach, and also facilitates melting and coating of the capsule material to prepare a higher-quality microcapsule powder. Moreover, a melting point range of 60-140° C. is preferred for the capsule material, while in a higher temperature range, many core materials (e.g., NADH and NADPH) to be coated may be damaged.

The capsule material of the present invention is selected from at least one of rice bran fatty alcohols and higher fatty alcohols with an atomic number of C of 12 or more.

First, higher fatty alcohols and rice bran fatty alcohols have favorable chemical stability, do not decompose in gastric acid, but decompose under the action of intestinal digestive enzymes in the intestine, thereby releasing internal core materials. Second, higher fatty alcohols and rice bran fatty alcohols have favorable stability at room temperature, and may ensure that the microcapsule powder has storage stability in an in vitro open environment. Third, higher fatty alcohols and rice bran fatty alcohols have appropriate melting points, so that the core material cannot be damaged when the higher fatty alcohols and rice bran fatty alcohols reach a melting state, and the capsule material can be easily melted and coated to prepare a high-quality microcapsule powder. In addition, rice bran fatty alcohols and higher fatty alcohols, especially octacosanol, triacontanol and dotriacontanol, can also be used as nutritional supplements, which not only ensures the safety of use, but also plays a role in nutritional supplement.

When used as a capsule material, rice bran fatty alcohols have great potentials for use in functional food, health food, medicine and cosmetics due to remarkable antifatigue, lipid lowering and sexual function improving effects, and have been accepted as a new resource food on Jun. 9, 2017 in China. However, due to low solubility, rice bran fatty alcohols are difficult to play excellent biological functions. Therefore, in the prior art, rice bran fatty alcohols are generally embedded in a capsule material with good water solubility, e.g., arabic gum.

In the present application, rice bran fatty alcohols are used as the capsule material of the microcapsule powder for the first time, and due to a melting point of 80-83° C. and good fluidity of the powder at room temperature, rice bran fatty alcohols can be used as the capsule material to protect the core material and play a role in water insulation, oxygen insulation and gastric acid resistance, thereby maintaining the stability of the core material, solving the problem of decomposition of the core material in gastric acid, and improving the absorption and utilization rates of the core material in the intestine.

When the capsule material is higher fatty alcohols, the higher fatty alcohols are preferably one or more of octacosanol, triacontanol and dotriacontanol. High fatty alcohols are stable in nature, resistant to oxidation, acid and alkali, and non-hygroscopic, and have good biodegradability and biological activity. High fatty alcohols usually exist in the form of white waxy solid, powder or scale-like crystal, etc. at room temperature. In addition, higher fatty alcohols are non-toxic, edible, insoluble in water as most organic substances, and soluble in organic solvents such as ethanol and acetone. When used as a capsule material, high fatty alcohols may achieve the same technical effect as the rice bran fatty alcohols.

In theory, the core material of the present application may be any material absorbed in the intestine or needed to function in the intestine.

Generally, a core material is a substance that is likely to be damaged by gastric juice and needs to be absorbed or take effect in the intestine. Coating with a capsule material may ensure that the substance that needs to be absorbed or take effect in the intestine does not decompose or melt in the stomach.

The core material is preferably at least one of reduced nicotinamide adenine dinucleotide (NADH) and reduced nicotinamide adenine dinucleotide phosphate (NADPH).

The mass ratio of the capsule material to the core material is preferably (70-90):(10-30). In combination with the ratio in the example, on the one hand, a higher coating amount of a core material may be ensured, and on the other hand, the coating rate of the core material may also be kept at a high level in an actual product.

In the examples of the present invention, the particle size of the microcapsule powder may be determined according to actual needs and preparation methods. In the present invention, the particle size of the microcapsule powder is preferably 1-1,000 μm.

Figure 1:
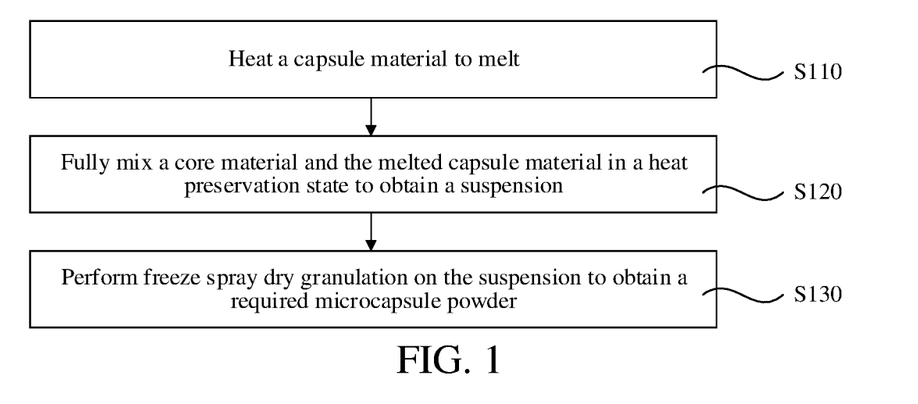
FIG. 1 is a flowchart of a freeze spray dry method for preparing a microcapsule powder.

Referring to FIG. 1, the present invention discloses a method for preparing the microcapsule powder according to the above technical solution, that is, a freeze spray dry method for preparing the microcapsule powder, including the following steps:

S110: Heat a capsule material to melt.

The capsule material has a melting point of greater than 42° C., and the capsule material does not decompose or dissolve under the action of protease and gastric acid, but decomposes under the action of intestinal digestive enzymes.

S120: Fully mix a core material and the melted capsule material in a heat preservation state to obtain a suspension.

Preferably, the operation of fully mixing a core material and the melted capsule material in a heat preservation state to obtain a suspension is: performing stirring at a rotation speed of 500-1,200 rpm for 3-10 min in a heat preservation state to obtain a suspension. S130: Perform freeze spray dry granulation on the suspension to obtain the microcapsule powder.

The prepared microcapsule powder includes the core material and the capsule material coated outside the core material.

Preferably, the operation of performing freeze spray dry granulation on the suspension is: performing freeze spray dry granulation on the suspension using a spray dryer.

Preferably, the spray dryer has the following parameters: the inlet air temperature is 2-20° C., the outlet air temperature is 15-30° C., the temperature in the middle of a chamber is 5-25° C., and the feed rate is 100-1,500 mL/min.

Figure 2:
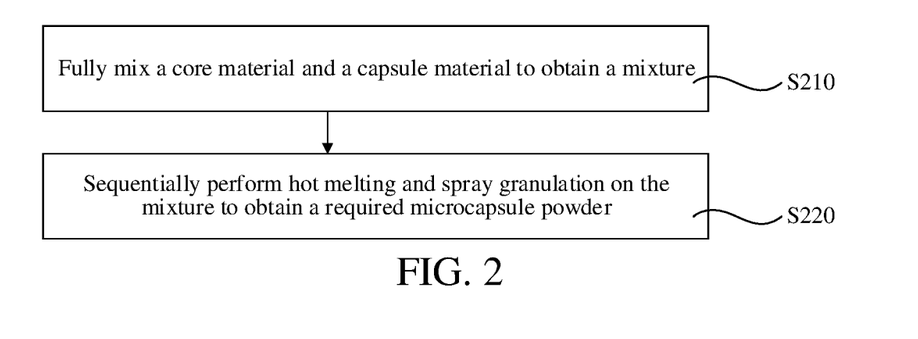
FIG. 2 is a flowchart of a hot melt mixing spray method for preparing a microcapsule powder.

Referring to FIG. 2, the present invention further discloses another method for preparing the microcapsule powder according to the above technical solution, that is, a hot melt mixing spray method for preparing the microcapsule powder, including the following steps:

S210: Fully mix a core material and a capsule material to obtain a mixture.

The capsule material has a melting point of greater than 42° C., and the capsule material does not decompose or dissolve under the action of protease and gastric acid, but decomposes under the action of intestinal digestive enzymes.

Preferably, the core material and the capsule material may be fully mixed using a mixer.

Preferably, the mixer has the following parameters: the mixing frequency is 25-40 Hz, and the mixing time is 30-60 min.

S220: Sequentially perform hot melting and spray granulation on the mixture to obtain the microcapsule powder.

The prepared microcapsule powder includes the core material and the capsule material coated outside the core material.

Preferably, the operation of sequentially performing hot melting and spray granulation on the mixture is: after heating the mixture to melt, performing spray granulation on the heated and melted mixture using an atomization system.

Preferably, the atomization system has the following parameters: the rotation speed of an atomizing wheel is 15,000-25,000 rpm, the inlet air temperature is 2-15° C., the outlet air temperature is 15-30° C., the temperature in the middle of a chamber is 5-10° C., and the feed rate is 100-1,500 mL/min.

In this implementation, in order to facilitate production, the operation of heating the mixture to melt is performed using a feed system of a hot melt extruder.

Figure 3:
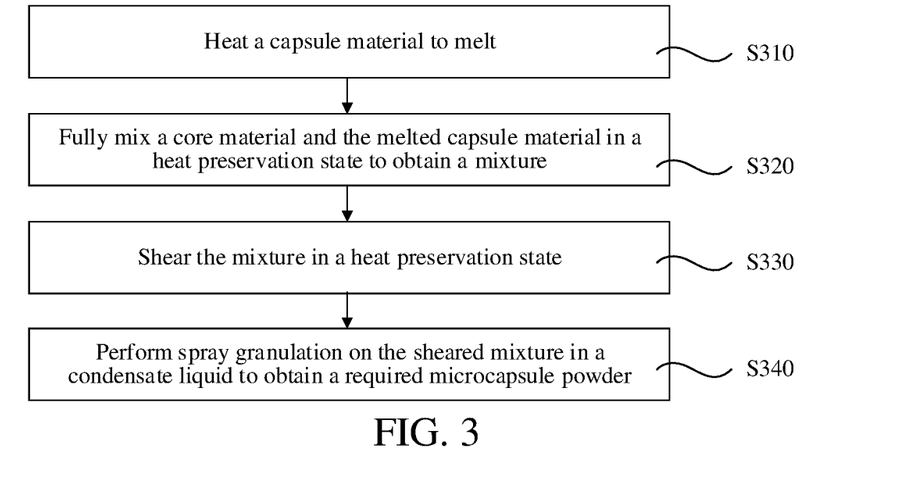
FIG. 3 is a flowchart of a condensation in liquid method for preparing a microcapsule powder.

Referring to FIG. 3, the present invention further discloses another method for preparing the microcapsule powder according to the above technical solution, that is, a condensation in liquid method for preparing the microcapsule powder, including the following steps:

S310: Heat a capsule material to melt.

The capsule material has a melting point of greater than 42° C., and the capsule material does not decompose or dissolve under the action of protease and gastric acid, but decomposes under the action of intestinal digestive enzymes.

S320: Fully mix a core material and the melted capsule material in a heat preservation state to obtain a mixture.

S330: Shear the mixture in a heat preservation state.

The shearing speed is 8,000-10,000 rpm, and shearing time is 6-15 min.

S340: Perform spray granulation on the sheared mixture in a condensate liquid to obtain the microcapsule powder.

The prepared microcapsule powder includes the core material and the capsule material coated outside the core material.

Preferably, the operation of performing spray granulation on the sheared mixture in a condensate liquid is performed in a condensation dryer.

Preferably, the condensation dryer has the following parameters: the rotation speed of a spray wheel is 15,000-25,000 rpm, the temperature of the condensate liquid is 10-20° C., and the feed rate is 100-1,500 mL/min.

Figure 4:
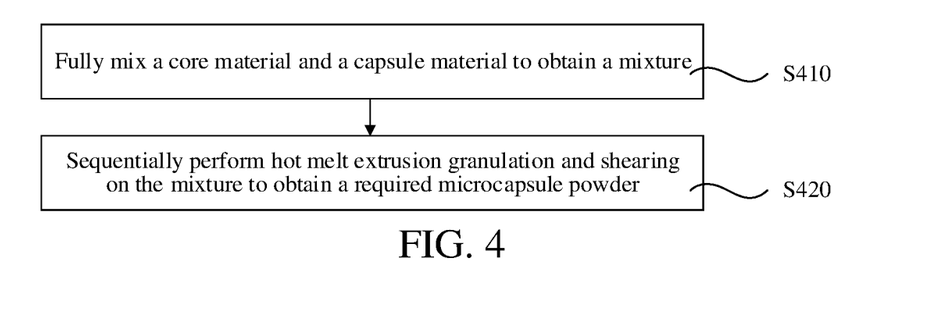
FIG. 4 is a flowchart of a hot melt extrusion method for preparing a microcapsule powder.

Referring to FIG. 4, the present invention further discloses another method for preparing the microcapsule powder according to the above technical solution, that is, a hot melt extrusion method for preparing the microcapsule powder, including the following steps:

S410: Fully mix a core material and a capsule material to obtain a mixture.

The capsule material has a melting point of greater than 42° C., and the capsule material does not decompose or dissolve under the action of protease and gastric acid, but decomposes under the action of intestinal digestive enzymes.

Preferably, the core material and the capsule material may be fully mixed using a mixer.

Preferably, the mixer has the following parameters: the mixing frequency is 25-40 Hz, and the mixing time is 30-60 min.

S420: Sequentially perform hot melt extrusion granulation and shearing on the mixture to obtain the microcapsule powder.

The prepared microcapsule powder includes the core material and the capsule material coated outside the core material.

Preferably, the shearing speed is 8,000-10,000 rpm.

Preferably, the operations of sequentially performing hot melt extrusion granulation and shearing on the mixture are: performing hot melt extrusion granulation on the mixture using a hot melt extruder, and then shearing the cooled hot melt extrusion granulated product using a shearing system.

Preferably, the hot melt extruder has the following parameters: the extrusion temperature is 100-120° C., the diameter of an extrusion die hole is 0.5-5 mm, and the extrusion speed is 5-150 rpm.

Specific examples are as follows.

Example 1

Preparation of Microcapsule Powder by Freeze Spray Dry Method 540 g of rice bran fatty alcohol was accurately weighed and put into a 1,000 mL jacketed kettle. The temperature of a water bath was kept at 80° C. until the rice bran fatty alcohol melted. 60 g of NADH was put into the melted rice bran fatty alcohol in a heat preservation state, and stirred at 500 rpm for 10 min to fully mix to obtain a suspension. Freeze spray dry granulation was performed on the suspension using a spray dryer. The spray dryer was adjusted to the working parameters as follows: an inlet air temperature of 2° C., an outlet air temperature of 15° C., a temperature in the middle of a chamber of 5° C., and a feed rate of 1,500 mL/min, to obtain a rice bran fatty alcohol coated NADH microcapsule powder, recorded as sample 1.

EXAMPLE 2

Preparation of Microcapsule Powder by Hot Melt Mixing Spray Method 480 g of rice bran fatty alcohol and 120 g of NADH were accurately weighed and put into a mixer. The mixer was started to work at a frequency of 25 Hz for 60 min to fully mix the rice bran fatty alcohol and the NADH. After mixing, the mixture was charged into a feed system of a hot melt extruder, melted at 140° C., and delivered to an atomization system to perform spray embedding granulation. At a rotation speed of an atomizing wheel of 15,000 rpm, an inlet air temperature of 2° C., an outlet air temperature of 15° C., a temperature in the middle of a chamber of 5° C., and a feed rate of 1,500 mL/min, a rice bran fatty alcohol coated NADH microcapsule powder was obtained and recorded as sample 2.

EXAMPLE 3

Preparation of Microcapsule Powder by Condensation in Liquid Method 420 g of rice bran fatty alcohol was accurately weighed and put into a 1,000 mL jacketed kettle. A water bath was heated to 90° C. to melt the rice bran fatty alcohol. 180 g of NADH was added to the melted rice bran fatty alcohol in a heat preservation state to obtain a mixture. High shear was performed on the mixture at 10,000 rpm. After 6 min, the jacketed kettle was connected to a condensation dryer containing a condensate liquid to perform spray granulation by condensation in liquid. At a rotation speed of a spray wheel of the condensation dryer of 25,000 rpm, a temperature of the condensate liquid of 10° C., and a feed rate of 1,500 mL/min, a rice bran fatty alcohol coated NADH microcapsule powder was obtained and recorded as sample 3.

EXAMPLE 4

Preparation of Microcapsule Powder by Freeze Spray Dry Method 540 g of triacontanol was accurately weighed and put into a 1,000 mL jacketed kettle. The temperature of a water bath was kept at 100° C. until the triacontanol melted. 60 g of NADPH was added to the melted triacontanol in a heat preservation state, and stirred for 3 min at 1,200 rpm to fully mix to obtain a suspension. Freeze spray dry granulation was performed on the suspension using a spray dryer. The spray dryer was adjusted to the working parameters as follows: an inlet air temperature of 20° C., an outlet air temperature of 30° C., a temperature in the middle of a chamber of 25° C., and a feed rate of 100 mL/min, to obtain a triacontanol coated NADPH microcapsule powder, recorded as sample 4.

EXAMPLE 5

Preparation of Microcapsule Powder by Hot Melt Mixing Spray Method 480 g of triacontanol and 120 g of NADPH were accurately weighed and put into a mixer. The mixer was started to work at a frequency of 40 Hz for 30 min to fully mix the triacontanol and the NADPH. After mixing, the mixture was charged into a feed system of a hot melt extruder, melted at 120° C., and delivered to an atomization system to perform spray embedding granulation. At a rotation speed of an atomizing wheel of 25,000 rpm, an inlet air temperature of 15° C., an outlet air temperature of 30° C., a temperature in the middle of a chamber of 10° C., and a feed rate of 100 mL/min, a triacontanol coated NADPH microcapsule powder was obtained and recorded as sample 5.

EXAMPLE 6

Preparation of Microcapsule Powder by Hot Melt Extrusion Method 420 g of triacontanol and 180 g of NADPH were accurately weighed and mixed in a mixer at 40 Hz for 30 min. Then the mixture was charged into a feed system of a hot melt extruder, hot melted and extruded, delivered into a forming system and cooled. After cooling, the mixture was delivered into a shearing system and sheared. At an extrusion temperature of 120° C., a diameter of an extrusion die hole of 0.5 mm, an extrusion speed of 150 rpm, and a shear speed of 10,000 rpm, the sheared powder was collected to obtain a triacontanol coated NADPH microcapsule powder, recorded as sample 6.

Test Example 1

Effect of Mass Ratio of Core Material to Capsule Material on Embedding Rate

As core materials NADH and NADPH are very soluble in water, while capsule materials rice bran fatty alcohols and higher fatty alcohols are insoluble in water, when the microcapsule powder prepared in the present application is put in water, the core materials that are not embedded may dissolve in water. The embedding rate of the core materials in the microcapsule powder may be calculated by detecting the content of the core materials in the water. Embedding rate of core material=(Theoretical embedding amount of core material in sample-Content of core material in effluent solution detected by HPLC)/Theoretical embedding amount of core material in sample. The theoretical embedding amount of the core material in the sample is the added amount of the core material in the sample.

Detection of contents of core materials NADH and NADPH by HPLC: 50 mg of a sample was accurately weighed and put into a 25 mL volumetric flask. 25 mL of a sodium bicarbonate solution with a concentration of 100 mmol/L was added to a constant volume. After unembedded NADH or NADPH was dissolved out by ultrasonic treatment for 30 min, 1 mL of a solution was taken from the volumetric flask respectively, filtered with a 0.22 μm membrane, and injected into an HPLC sampling bottle. The content of NADH or NADPH in the sample solution was detected and calculated by HPLC. The detection and analysis by HPLC have the following parameters: Agilent 1260 Infinity II, including a quaternary pump, an automatic sampler, a column thermostat and a variable wavelength detector (VWD); separation column ChromCore AQ C18 (5 μm) 4.6×250 mm; and detection wavelength 260 nm. Specific parameters of detection for NADH and NADPH are shown in Table 1.

TABLE 1

Specific parameters of detection for contents of NADH and NADPH by HPLC

|   | Column temperature | Mobile phase | Flow rate | Retention time |
|---|---|---|---|---|
| NADH | 30° C. | 0.1 mol/L phosphate buffer with pH 6.6, chromatographic grade acetonitrile | 1 mL/min | 7.11 min |
| NADPH | 20° C. | Mobile phase A: 10 mM $NaH_2PO_4$ buffer solution; mobile phase B: 100% methanol | 0.7 mL/min | 10.62 min |

The detection results of the embedding amounts of the core materials in samples 1-6 in the examples are shown in Table 2. It can be seen that when the mass ratio by percentage of the core materials to the capsule materials is (10-30):(70-90), the embedding rate is above 93%, and the embedding effect is favorable.

TABLE 2

Embedding amounts and embedding rates of core materials in samples 1-6

| Sample name | Theoretical embedding amount of core material in sample (mg) | Amount of core material detected (mg) | Actual embedding amount (mg) | Embedding rate |
|---|---|---|---|---|
| Sample 1 | 5 | 0.04 | 4.96 | 99.2% |
| Sample 2 | 10 | 0.17 | 9.87 | 98.3% |
| Sample 3 | 15 | 0.795 | 14.205 | 94.7% |
| Sample 4 | 5 | 0.07 | 4.93 | 98.6% |
| Sample 5 | 10 | 0.21 | 9.79 | 97.9% |
| Sample 6 | 15 | 0.92 | 14.08 | 93.8% |

Test Example 2

Stability Test in Open Environment at Room Temperature 2 g of sample 2 and 2 g of sample 5 of the examples were taken respectively and placed in an open environment at room temperature for 7 days. The appearances were observed first. Then, 50 mg of sample 2 and 50 mg of sample 5 stood for 7 days were weighed respectively and put in 50 mL centrifuge tubes. 45 mL of xylene was added, and the centrifuge tubes were shaken continuously for 30 min with the caps tightened. Then the liquids in the centrifuge tubes were completely transferred into 125 mL separating funnels. About 80 mL of a sodium bicarbonate solution with a concentration of 100 mmol/L was added into the separating funnels, and the mixed solutions were extracted continuously by shaking for 30 min and then allowed to stand for 5-10 min. After the liquids completely were separated into layers, the lower solutions were taken and put into 100 mL volumetric flasks, then diluted to a constant volume of 100 mL with a 100 mmol/L sodium bicarbonate solution, and shaken well. The contents of the core materials in the samples were detected respectively by the same detection method as in Test Example 1.

Retention rate of core material=Content of core material detected in sample/Theoretical embedding amount of core material in sample. The theoretical embedding amount of the core material in the sample is the added amount of the core material in the sample. The results are shown in Table 3.

TABLE 3

Retention results of core materials in samples in open environment at room temperature

| Sample name | Appearance before placement | Appearance after placement | Theoretical embedding amount of core material in sample (mg) | Content of residual core material detected in each sample (mg) | Retention rate of core material |
|---|---|---|---|---|---|
| Sample 2 | Light yellow powder | Yellow powder | 5 | 4.93 | 98.6% |
| Sample 5 | White powder | Yellowish powder | 10 | 9.75 | 97.5% |

It can be seen from the results in Table 3 that the retention rate of the core material of the microcapsule powder prepared by the present invention reached 97% or higher after being placed in an open environment at room temperature for 7 days, indicating that the microcapsule powder of the present invention may effectively isolate moisture and oxygen in the air from the core material, thereby greatly improving the stability of the core material, and broadening the industrial application prospect of the core material.

Test Example 3

Release Test in Simulated Gastric Acid Solution

A Tablet Four-Usage Tester was started for preheating. The temperature was set at 37° C. A basket shaft and a basket were installed. A positioning ball used for positioning (marked) was put into a dissolution cup (900 mL of a hydrochloric acid solution with pH 1.2 was added into each dissolution cup) and fixed. 200 mg of sample 2 and 200 mg of sample 5 in the examples were taken respectively, wrapped with gauze and put into corresponding baskets. After being rotated at 100 r/min for 4 h, 1 mL of liquid was taken from each of the dissolution cups. The contents of the core materials in the samples were detected by the same detection method as in Example 1.

Retention rate of core material=(Theoretical embedding amount of core material in sample-Content of core material in hydrochloric acid solution detected)/Theoretical embedding amount of core material in sample. The theoretical embedding amount of the core material in the sample is the added amount of the core material in the sample. The calculated results are shown in Table 4. It can be seen that after 4 h in a strong acid environment, the retention rates of the core materials in sample 2 and sample 5 were still 90% or higher, and the acid resistance effects were excellent, proving that the core materials were not released in a gastric juice environment.

TABLE 4

Retention results of core materials in samples in simulated gastric juice

| Sample name | Retention rate of core material before test | Dissolution rate of core material | Retention rate of core material after test |
|---|---|---|---|
| Sample 2 | 98.3% | 5.2% | 94.8% |
| Sample 5 | 97.9% | 7.7% | 92.3% |

Test Example 4

Release Test in Artificial Intestinal Juice

A Tablet Four-Usage Tester was used for testing. The tester was started for preheating. The temperature was set at 37° C. A basket shaft and a basket were installed. A positioning ball used for positioning (marked) was put into a dissolution cup (900 mL of prepared artificial intestinal juice was added into each dissolution cup) and fixed. 200 mg of sample 2 and 200 mg of sample 5 in the examples as well as 200 mg of corresponding core materials were taken respectively, wrapped with gauze and put into corresponding baskets. After being rotated at 100 r/min for 1, 2, 3 and 4 h, 1 mL of liquid was taken from each of the dissolution cups. The contents of the core materials in the samples were detected by the same detection method as in Example 1.

Retention rate of core material=(Theoretical embedding amount of core material in sample-Content of core material in artificial intestinal juice detected)/Theoretical embedding amount of core material in sample. The theoretical embedding amount of the core material in the sample is the added amount of the core material in the sample. The calculated results are shown in Table 5. After 1 h in the artificial intestinal juice environment, the dissolution rates of the core materials in sample 2 and sample 5 were 85% or higher, and after 3 h, the dissolution rates of the core materials in sample 2 and sample 5 were 95% or higher, indicating that the capsule materials of the microcapsule powder of the present application can successfully decompose in the intestine to ensure that the core material is absorbed by the intestine or takes effect in the intestine.

TABLE 5

Dissolution results of core materials in samples in artificial intestinal juice

| Sample name | Retention rate of NADH before test | Dissolution rate of core material after 1 h | Dissolution rate of core material after 2 h | Dissolution rate of core material after 3 h | Dissolution rate of core material after 4 h |
|---|---|---|---|---|---|
| Sample 2 | 98.3% | 87.4% | 91.5% | 95.2% | 97.1% |
| Sample 5 | 97.9% | 88.4% | 93.7% | 95.2% | 96.4% |
| NADH | 100% | 99.6% | 99.5% | 99.4% | 99.5% |
| NADPH | 100% | 98.4% | 99.7% | 99.3% | 99.1% |

Test Example 5

Accelerated Stability Test

Sample 2 and sample 5 in the examples were put into accelerated chambers at 37° C., 75% humidity. A product stability test was performed on the two groups of samples for 1, 2 and 3 months. At the 0th, 1st, 2nd and 3rd month, 50 mg of sample 2 and 50 mg of sample 5 were weighed respectively and put in 50 mL centrifuge tubes. 45 mL of xylene was added, and the centrifuge tubes were shaken continuously for 30 min with the caps tightened. Then the liquids in the centrifuge tubes were completely transferred into 125 mL separating funnels. About 80 mL of a sodium bicarbonate solution with a concentration of 100 mmol/L was added into the separating funnels, and the mixed solutions were extracted continuously by shaking for 30 min and then allowed to stand for 5-10 min. After the liquids completely were separated into layers, the lower solutions were taken and put into 100 mL volumetric flasks, then diluted to a constant volume of 100 mL with a 100 mmol/L sodium bicarbonate solution, and shaken well. 1 mL of the above samples were pipetted respectively. The contents of the core materials in the samples were detected by the same detection method as in Example 1.

Retention rate of core material=Content of core material detected in sample/Theoretical embedding amount of core material in sample. The theoretical embedding amount of the core material in the sample is the added amount of the core material in the sample. The results are shown in Table 6. After three months of acceleration, the retention rates of the core material contents of the two groups of samples decreased slightly, but both were 90% or higher, meeting the product qualification standard of general accelerated tests, indicating that the microcapsule powder prepared by the present invention had favorable stability.

TABLE 6

Retention results of core materials in samples after accelerated stability test

| Sample name | Retention rate of core material at 0th month | Retention rate of core material at 1st month | Retention rate of core material at 2nd month | Retention rate of core material at 3rd month |
|---|---|---|---|---|
| Sample 2 | 98.3% | 95.0% | 94.1% | 92.5% |
| Sample 5 | 97.9% | 93.8% | 92.3% | 90.8% |

What is claimed is:

1. A microcapsule powder stable in gastric acid, comprising a core material and a capsule material coated outside the core material, wherein the capsule material has a melting point of greater than 42° C., and the capsule material does not decompose or dissolve under the action of protease and gastric acid, but decomposes under the action of intestinal digestive enzymes;
the capsule material is rice bran fatty alcohol;
the core material is selected from at least one of reduced nicotinamide adenine dinucleotide and reduced nicotinamide adenine dinucleotide phosphate; and
the microcapsule powder has a particle diameter of 1-1,000 μm.

2. The microcapsule powder according to claim 1, wherein the capsule material has a melting point of 60-140° C.

3. The microcapsule powder according to claim 1, wherein a mass ratio of the capsule material to the core material is (70-90):(10-30).

4. A method for preparing the microcapsule powder according to claim 1, comprising the following steps:
heating the capsule material to melt, wherein the capsule material has a melting point of greater than 42° C., and the capsule material may not decompose or dissolve under the action of protease and gastric acid, but decomposes under the action of intestinal digestive enzymes;
fully mixing the core material and the melted capsule material in a heat preservation state to obtain a suspension of particles of the core material in the melted capsule material; and
performing freeze spray dry granulation on the suspension to obtain the required microcapsule powder, wherein the microcapsule powder comprises the core material and the capsule material coated outside the core material.

5. A method for preparing the microcapsule powder according to claim 1, comprising the following steps:
fully mixing the core material and the capsule material to obtain a mixture, wherein the capsule material has a melting point of greater than 42° C., and the capsule material may not decompose or dissolve under the action of protease and gastric acid, but decomposes under the action of intestinal digestive enzymes; and
sequentially performing hot melting and spray granulation on the mixture to obtain the required microcapsule powder, wherein the microcapsule powder comprises the core material and the capsule material coated outside the core material.

6. A method for preparing the microcapsule powder according to claim 1, comprising the following steps:
heating the capsule material to melt, wherein the capsule material has a melting point of greater than 42° C., and the capsule material may not decompose or dissolve under the action of protease and gastric acid, but decomposes under the action of intestinal digestive enzymes;
mixing the core material and the incited capsule material in a heat preservation state to obtain a mixture;
shearing the mixture in a heat preservation state at a speed of 10,000-16,000 rpm for 6-15 min; and
performing spray granulation on the sheared mixture in a condensate liquid to obtain the required microcapsule powder, wherein the microcapsule powder comprises the core material and the capsule material coated outside the core material.

7. A method for preparing the microcapsule powder according to claim 1, comprising the following steps:
fully mixing the core material and the capsule material to obtain a mixture, wherein the capsule material has a melting point of greater than 42° C., and the capsule material may not decompose or dissolve under the action of protease and gastric acid, but decomposes under the action of intestinal digestive enzymes; and
sequentially performing hot melt extrusion granulation and shearing on the mixture to obtain the required microcapsule powder, wherein the shearing speed is 8,000-10,000 rpm, and the microcapsule powder comprises the core material and the capsule material coated outside the core material.

* * * * *